United States Patent [19]

Anderson, II et al.

[11] Patent Number: 5,677,187
[45] Date of Patent: Oct. 14, 1997

[54] TAGGING CHEMICAL COMPOSITIONS

[76] Inventors: David K. Anderson, II, 15110 Benfer Rd., Houston, Tex. 77069; Manuel E. Gonzalez, 5305 Windy Lake, Kingwood, Tex. 77345; Nicholas Paul Valenti, 2047 Riverlawn Dr., Kingwood, Tex. 77339

[21] Appl. No.: 469,226

[22] Filed: Jun. 6, 1995

Related U.S. Application Data

[63] Continuation-in-part of Ser. No. 108,625, filed as PCT/US93/00647, Jan. 25, 1993, Pat. No. 5,474,937, and a continuation-in-part of Ser. No. 825,478, Jan. 29, 1992, abandoned.

[51] Int. Cl.⁶ ................................... G01N 33/24
[52] U.S. Cl. ...................... 436/27; 436/56; 436/106
[58] Field of Search ..................... 436/27, 56, 106, 436/110, 166

[56] References Cited

U.S. PATENT DOCUMENTS

| | | | |
|---|---|---|---|
| 3,733,178 | 5/1973 | Eriksen | 436/56 |
| 3,772,099 | 11/1973 | Ryan et al. | 250/83 R |
| 3,897,284 | 7/1975 | Livesay | 149/21 |
| 4,013,490 | 3/1977 | Ryan et al. | 149/2 |
| 4,018,635 | 4/1977 | Ryan et al. | 250/301.1 R |
| 4,197,104 | 4/1980 | Krystyniak et al. | 65/21 |
| 4,198,307 | 4/1980 | Berkowitz et al. | 252/62.54 |
| 4,306,993 | 12/1981 | Danielson et al. | 252/316 |
| 4,359,353 | 11/1982 | Kydd | 149/2 |
| 4,363,678 | 12/1982 | Nishimura et al. | 149/6 |
| 4,399,226 | 8/1983 | Danielson et al. | 436/56 |
| 4,455,179 | 6/1984 | Yamaguchi et al. | 149/109.6 |
| 4,469,623 | 9/1984 | Danielson et al. | 252/408.1 |
| 4,470,855 | 9/1984 | Bampfield | 149/2 |
| 4,537,645 | 8/1985 | Yamaguchi et al. | 149/3 |
| 4,640,035 | 2/1987 | Kind et al. | 40/625 |
| 5,059,261 | 10/1991 | Condo et al. | 149/19.92 |
| 5,292,387 | 3/1994 | Highsmith et al. | 149/19.1 |
| 5,474,937 | 12/1995 | Anderson et al. | 436/27 |

FOREIGN PATENT DOCUMENTS 9315398   8/1993   WIPO ..................... G01N 30/02

*Primary Examiner*—Lyle A. Alexander
*Attorney, Agent, or Firm*—John R. Casperson

[57] ABSTRACT

Rare elements, which can be selected from Ni, Cu, W, Li, N, Ce, Sn, Y, Nd, Nb, Co, La, Pb, Ga, Mo, Th, Cs, Ge, Sm, Gd, Be, Pr, Se, As, Hf, Dy, U, B, Yb, Er, Ta, Br, Ho, Eu, Sb, Tb, Lu, Tl, Hg, I, Bi, Tm, Cd, Ag, In, Se, Pd, Pt, Au, He, Te, Rh, Re, Ir, Os, and Ru can be used to tag commodities, including explosive materials, with a unique tagging agent.

11 Claims, No Drawings

TAGGING CHEMICAL COMPOSITIONS

This application is a continuation-in-part of application Ser. No. 08/108,625, filed under 35USC§371 on Aug. 30, 1993 now U.S. Pat. No. 5,474,937 from PCT application Ser. No. PCT/US93/00647, filed Jan. 25, 1993 and claiming a priority as a continuation-in-part from U.S. application Ser. No. 07/825,478, filed Jan. 29, 1992, now abandoned.

Contamination of water with potentially hazardous materials is a common problem facing industry, the government and the general public. As a result of spills in waterways, leakage from storage facilities and surface discharges, contaminants are slowly destroying our water supply. Such contaminants may further enter our water supplies via subsurface soil and/or rock formations and eventually percolate into the groundwater. There are over two hundred organic and inorganic chemicals which have been identified in various groundwater supplies alone. Such ground water is the principal source of municipal water, agricultural irrigation, and water used by industry. There is thus a consistent health threat to our drinking water supplies. In addition, chemical discharging into intercoastal waters has resulted in damage to marine life as well as to marine ecosystems.

It is a fairly common occurrence to find such contaminants in our nation's lakes and rivers as well as the surrounding oceans. The amount of unlawful dumping of such wastes is increasing in the waters of the United States. Our groundwater, drinking water and waste water continues to be jeopardized as such activities continue. Useful methods of ascertaining the source of such pollutants into our waterways is essential.

Clearly there is a long felt need by the public for a safe technique for "serializing" or "fingerprinting" petroleum, petroleum products and bulk chemicals in storage or transit so that responsibility for dumping, spilling or leakage of such chemicals can be appropriately determined. There is also a need for serializing bulk adulterants such as cyanides which are sometimes placed in foods and medicines by disturbed people to aid in apprehending such people. There is also a long felt need by the petroleum and chemical industry for safe techniques to serialize oil and other chemical products for internally auditing the transfer of such products to prevent and/or prove theft.

It has been proposed to use radioactive materials as tracers in fluids. However, the use of radioactive materials for fingerprinting liquids would not be totally satisfactory. The consumption of petroleum products containing radioactive tracers, for example, would result in their uncontrolled release into the environment. It has also been proposed to use certain non-radioactive tracers in reservoir characterization studies to determine fluid residence times and conductive fluid flow paths. However, in such applications, the tracer is detected in salt water. Salt water is a very simple chemical composition and it is easy to obtain a low detection threshold because there are not many interfering materials. However, our proposals to label crude oil and other chemical materials with low levels of non-radioactive tagging agents have been met with skepticism because of the presumed difficulties in detecting such tagging agents. We have found that it is not difficult to identify many non-radioactive materials at very low levels if one knows what one is looking for.

Another long felt need by law enforcement authorities and by manufacturers of explosives and materials which can be used in explosives, such as ammonium nitrate, is for a technique for determining the origin of an explosive material which has been used in criminal activity. Law enforcement is concerned with establishing culpability for activities such as shootings or bombings, while manufacturers are concerned with establishing a lack of culpability in product liability cases. A technique which can be used to establish the manufacturer's identity and sales location in a particular case involving the use of explosive materials would be very desirable.

It has been proposed to label particulate materials, such as gunpowder or ammonium nitrate, with macroscopic particles bearing a manufacturer's code. However, these techniques are expensive and the effect of macroscopic particles in the explosion process has not been fully established. Also, it is technically difficult to incorporate macroscopic particles into particulate materials in such a way that a stable and uniform distribution can be obtained. An inexpensive technique to incorporate a tagging agent into a particulate material in a stable and uniform manner and in such a way to alleviate concerns relating to possible negative interactions between the tagging agent and the tagged material would be very desirable.

SUMMARY OF THE INVENTION

In one embodiment of the invention, there is provided a chemical composition which contains a tagging agent dispersed therein. The tagging agent contains at least two different rare elements of the periodic table which are foreign to the chemical composition and are present in the chemical composition in a detectable amount and at a naturally occurring isotopic distribution.

Because there are a large number of rare elements, there is an extremely large number of possible subcombinations of rare elements. It is therefore feasible to assign distinct subcombinations of rare elements to chemical commodities, based on batch or chemical manufacturer, for example. Using existing analysis technology, it is relatively easy to perform an elemental analysis to determine the elemental identity of any foreign elements present, even at extremely low concentrations. Thus only low levels of the tagging agent need be used. The manufacturer of a particular commodity which has used the tagging technology of the invention and kept records will thus in a good position to prove or disprove whether a particular commodity originated with them. From a law enforcement perspective, a database containing the subcombinations of rare elements employed as tagging agents by particular manufacturers would enable the source of a particular commodity to be quickly determined.

In another embodiment of the invention, there is provided a method for tagging a chemical composition with a tagging agent. The method is carried out by dispersing a tagging agent throughout the chemical composition. The tagging agent contains at least two different rare elements of the periodic table which are foreign to the chemical composition. Each rare element is dispersed in the chemical composition in a detectable amount and has a natural isotopic distribution. The method is well adapted for producing the composition containing the tagging agent previously discussed.

In another embodiment of the invention, there is provided a composition of matter which is useful as a tagging agent. The composition comprises a carrier liquid containing soluble forms of at least two different rare elements. The rare elements are selected from the periodic table and have a naturally occurring isotopic distribution. The soluble forms of the rare elements are dissolved in the carrier liquid. The rare elements are dissolved in the carrier liquid at a concentration in the range of from about 1 ppm to about 100,000 ppm, based on elemental weight. The composition is well suited for use in the method previously discussed.

In another embodiment of the invention, there is provided a method for forming a tagged chemical composition. In the method, elemental analysis results for a chemical composition are provided to indicate the concentrations of rare elements in the chemical composition. A combination of rare elements is then added to the chemical composition to form a tagged chemical composition. The rare elements are added to the chemical composition in amounts sufficient so that the combination of rare elements added to the chemical composition can be subsequently determined by an elemental analysis of the tagged chemical composition. This is simplest to accomplish when the rare elements which have been added are present in the chemical composition prior to the addition of at near zero concentrations.

Incorporating tagging agents into particulate materials has been technically difficult. By use of the present method, the tagging agent is extremely well dispersed, for practical purposes at the atomic level. The method is also extremely simple and inexpensive to carry out, even where the composition is a particulate solid. For example, the rare elements can be added to the composition in the form of a solution which can be slurried with the composition or sprayed onto the composition. Separation problems are thus eliminated, and potential problems caused by interactions between the particulate material and the tagging agent, such as in an explosion process, are reduced if not eliminated, since extremely low levels of the rare elements can be added.

In another embodiment of the invention, there is provided a method for determining the source of explosive material which has been used in an explosion. The explosion forms a blast residue. The method is carried out by collecting a portion of the blast residue. The collected portion is analyzed to identify a combination of rare elements present in the blast residue. The thus identified combination of rare elements in the blast residue is correlated with a combination of rare elements which have been used in a tagged explosive material. The source of the tagged explosive material can then be determined, based on the combination of elements present.

Blast residue contains explosion products as well as unreacted explosive material. The blast residue is concentrated at ground zero in the case of a bomb, being driven into the earth, and in powder burns found on close range gunshot victims. The residue is thus often collectable. Where the tagging agents of the invention have been employed, the origin of the explosive material employed can often be determined.

DETAILED DESCRIPTION OF THE INVENTION

The invention pertains to a method for identifying the source of a transported chemical shipment. The method may be employed to verify that a sample received by an individual is identical to the sample that was shipped. In addition, the invention may be employed to detect the source of a newly introduced contaminant in a source, such as a water supply.

The method employs a non-radioactive chemical isotope which, with the material being transported, is introduced into the storage container prior to the container being loaded onto a freight vessel. Either non-radioactive chemical elements or non-radioactive inorganic or organic compounds may be employed. The amount of isotopic compound introduced into the storage vessel may be less than one part per billion (ppb) of the chemical being transported. For certain isotopic compounds, the amount of isotopic compound introduced is between about 1 to about 5 ppb of the chemical being transported.

The invention finds particular applicability for marking chemical samples. Marking of the sample permits the recipient of the cargoed product to verify that the sample received is identical to the sample that was shipped. In this embodiment of the invention, the non-radioactive isotope substance is admixed with the chemical to be transported prior to shipment of the chemical. Upon arrival at its destination point, the chemical shipment is analyzed. Matching the isotopic compound with the isotopic compound introduced into the storage vessel prior to shipment is indicative that the shipped chemical is identical to the chemical received. The invention has applicability in the shipment of any chemical commodity, regardless of method of shipping or chemical structure of the commodity.

The method has particular applicability in the shipment of crude oil, refined oil, grains, processed and unprocessed chemicals as well as with bulk refined products. In addition, the invention may be employed in the shipment of a pollutant, hazardous material or a toxic material. As such, the invention has particular applicability in the identification of spilled shipments of spilled oil, pesticides, cyanide based compounds, arsenic containing compounds, dioxin, military chemical agents, military biological agents, naphthalene and biphenols.

The chemical substance may be a non-radioactive isotope of the chemical shipment being transported. Any element or compound which can be produced with stable isotopes not generally found in nature is suitable for the chemical substance. The substance is labeled with a non-radioactive atom at least one specific site in the molecule. Particularly preferred are those compounds deuterated or rendered isotopic by carbon-13 or fluorine-19. Also preferred are nitrogen-15, oxygen-17 and oxygen-18 isotopic materials.

The chemical substance is more commonly a non-radioactive isotope of such organic solvents as acetone, acetonitrile, benzene, bromobenzene, chlorobenzene, chloroform, cyclohexane, dichlorobenzene, trichloroethylene, diethylether, diglyme, dimethylsulfoxide, dioxane, ethanol, methanol, methylene chloride, nitrobenzene, octane, pyridine, tetrachloroethane, tetrahydrofuran, tetrametholsilane, toluene, trifluoroacetic acid, trifluoroethyl alcohol, xylene, ammonium bromide, or acetyl chloride.

Common inorganic deuterated solvents include deuterium oxide, ammonium deuteroxide, and deuterated ammonium sulfate. In addition, the non-radioactive isotope may be derived from an organometallic material. Isotopes of organometallic and inorganic compounds may include those containing iron-57, europium-151, and tin-119.

One particularly preferred class of organic compounds are those which have been deuterated, i.e., wherein the hydrogen atoms covalently bound to carbon atoms are replaced with deuterium atoms. Deuterium is a non-radioactive isotope of hydrogen which is often called heavy hydrogen. Deuteration of organic compounds can be accomplished by methods known in the art such as those disclosed in U.S. Pat. Nos. 3,746,634 and 3,876,521 wherein deuteration is effected with deuterium gas in the presence of a Group VII or VIII metal catalyst at a temperature between about 100 and about 300 degrees C. The non-radioactive isotopes for use in this invention may further be prepared in accordance with the prior art teachings of such materials used in the medical arts.

The non-radioactive chemical substance may have the heavy atom in any position of the molecule. Likewise, one or more of the reactive sites of a molecule may contain a heavy atom. For example, the number of permutations possible with n-octane is in the thousands since one or all of the hydrogen atoms of the molecule may be substituted with deuterium as set forth below:

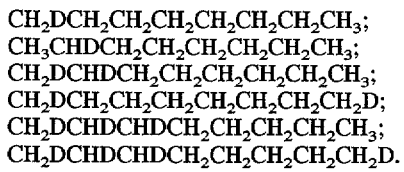

The number of uniquely identifiable combinations of deuterated n-octanes naturally decreases the chance that more than one shipping vessel will contain the same non-radioactive isotope.

The method of this invention may further be employed for the identification of source of non-radioactive materials infiltrating water supplies. The method has particular applicability where the substance infiltrating the water supply is environmentally toxic and hazardous. By this process, a non-radioactive isotope of a chemical substance is introduced into a storage vessel containing the chemical supply to be transported prior to loading of the storage vessel onto the freight cargo leaving the exit port. When spills of the transported chemical are suspected, a sample of contaminated water is recovered from the water supply. The sample is then analyzed. Detection of the non-radioactive isotope in the contaminated sample is indicative of the source of the spill. The chemical substance may be a non-radioactive isotope of the chemical shipment being transported.

Suitable as the chemical substance used in the detection of the polluting source are those set forth above.

Still further the method of this invention may be employed to identify the source of chemical leakage from a land-based storage tank containing such a contaminant. The situs of the leakage may be either a water body or terrain. The presence of the contaminant is effectuated by recovering a sample of the contaminated area and analyzing the sample for the presence of the non-radioactive isotope to determine the location of the particular land-based storage tank which is leaking.

Isotopic identification may be readily achieved by mass spectroscopy, nuclear magnetic resonance spectroscopy or gas chromatography analysis. For instance, the spectra or retention time of the labelled isotope [prior to being introduced into the vessel containing the desired (ordered) chemical] may be compared to the spectra or retention time of the contaminant present in the water supply. See further B. B. McInteer et al., "The ICONS Facility: Separating Nitrogen and Oxygen Isotopes at Los Alamos", *Los Alamos Technical Bulletin*, March 1988.

In further embodiments of the invention, fluid compositions can be labeled or tagged by incorporating custody tag or custody tag modifiers therein. The fluid compositions are generally gases or liquids. The liquids are generally classified as oil based or water based. Oil based liquids generally include petroleum, and petroleum products. Volatile custody tags and custody tag modifiers are used to tag gases. Oil soluble custody tags and custody tag modifiers are generally used to tag oil based liquids. Water soluble custody tags and custody tag modifiers are generally used to label water based liquids. The custody tags are integral with the fluids and are nearly impossible to remove.

The amount of custody tag or tag modifier incorporated into the fluid can vary over a wide range. However, the tagging agent should always be added in an amount sufficient to be detected in the tagged product. Because the labeled fluids may be diluted a great deal with other materials before a sample is taken for analysis it can be desirable to incorporate a relatively large amount of custody tag into the fluid, although the amount used will generally be below about 1 ppm for economic reasons. On the other end of the scale, using current technology, certain tagging agents can probably be detected at levels of a few parts per trillion in gases and simple water solutions. The amount of custody tag employed in oil based liquids will generally be between these two ranges. Often, the custody tag will be used in an oil based liquid at below the 500 ppb level. In many instances, a concentration of custody tag in the range of 1 to 100 ppb will give desirable results.

The custody tag can be added to the fluid using a variety of techniques, depending on how well dispersion is expected. For example, the custody tag can be metered into a stream as it flows through a line. This will generally provide a better result than simply dumping the custody tag into a large storage tank, for example. However, an oil tanker can be treated by pouring the custody tag in the hold and then filling the tanker with oil. It is preferred to add the custody tag continuous to the fluid through a method system at a transfer or storage facility.

Generally speaking, a custody tag will comprise at least two tagging agents, preferably three or more. Custody tag modifiers comprise at least one tagging agent, preferably only one. A custody tag modifier can be used to relabel a fluid containing a custody tag to indicate, for example, a transfer of custody. Preferably, the tagging agent present in a custody tag modifier is different from any of the tagging agents in the custody tagged fluid being relabeled.

Tagging agents suitable for use can generally be described as non-radioactive compounds which are not naturally occurring and which are identifiable in tagged fluids at low thresholds of detection. Besides the tagging agents listed above, another example of suitable materials is the class of halogenated hydrocarbons, such as chlorinated and/or fluorinated alkenes, alkanes and aromatics. These materials are easily detected at low concentrations using gas chromatography techniques coupled with ion traps and/or mass spectrometer techniques. Preferably, the tagging agents used can be detected in the fluid which contains them at concentrations of less than 500 ppb, such as in the 1–100 ppb range. It is desirable to assemble a library or collection of suitable tagging agents and make selections from said library to formulate custody tags based on compatibility of the tagging agents with the fluid to be tagged and the use of a unique tag. Compatibility is rather easy to determine and is based on the range of properties of the fluid to be transported or stored. It does not require an especially large collection of tagging agents to accomplish the capability to provide unique combinations. For example, 1,000 tagging agents can be used to formulate over 41 billion unique 3-component custody tags. Where the goal is to police dumps, spills and leaks, a record should be made of the custody tags which have been assigned to individual companies or shipments. The records should be gathered or complied into a database. The database can be referred to in the event of a spill, leak or dump to assign responsibility.

The presently preferred analysis technique for the detection of tagging agents utilizes a gas chromatograph coupled with a mass spectrometer although other chromatographic techniques can be used as well. It is first necessary, of course, to obtain a sample of the material to be analyzed for the presence of tagging agents. The sample is formed into a gas chromatograph stream and the stream is then flowed through the gas chromatograph. Predetermined portions of the stream are trapped and analyzed for tagging agent. Generally speaking, the analysis is carried out with a mass spectrometer. For difficult separations, the trapped portions of the sample are formed into a second stream and flowed through a second gas chromatograph. Predetermined portions of the second gas stream are trapped and analyzed for tagging agent. The determination of which portions of the chromatograph stream to trap is generally made before the original analysis of the sample and is usually based on retention time. It is made using knowledge of the tagging agent collection from which the tagging agents were selected, sometimes after a calibration run using known combinations of tagging agents from the collection.

Besides product tracking, one of the more important uses of the invention is expected to be in proving the innocence of environmental wrongdoing. Suppose a company is suspected or accused of contributing to the amount of noxious materials present at the site of a dump, spill or leak. Proving lack of culpability would be much easier with the use of custody tags.

A sample of the material should first be obtained and then analyzed to determine whether any tagging agents are present. If no tagging agents were found, the company should be able to establish lack of culpability if it could show that it routinely used tagging agents during the time period in question. If tagging agents were found, the company should be able to establish lack of culpability if it used different tagging agents than those that were found, or if it required its transferees of the material to use the tagging agents that were found.

In another embodiment of the invention, there is provided a chemical composition which contains a tagging agent dispersed therein. The tagging agent contains at least two different rare elements of the periodic table which are preferably foreign to the chemical composition and are present in the chemical composition in a detectable amount and at natural isotopic distribution. Although most any chemical composition can be tagged in this manner, the invention is especially well suited for tagging chemical commodities, especially particulate materials, including those particulate materials for which an identification of source may be desirable after the materials have been converted to another form. Because the tagging agents are elemental in form, they will generally survive chemical conversion processes, such as combustion or explosion. The tagging agents are thus highly suitable for tagging explosives, which are often nitrates, or explosive precursors, such as ammonium nitrate, which is available at purity levels in excess of 99 wt %.

By foreign to the chemical composition, it is meant that the rare elements used in the tagging agent are either not normally detectable at all in the composition being tagged or are detectable at extremely low levels. Generally speaking, the tagging agent should be selected so that it is easy to determine whether it is present at above background levels in the particular composition. This eliminates the need for quantitatively analyzing for the tagging agent and greatly simplifies use of the invention. The most preferred rare elements for a particular composition will be those which are not normally present in the composition in detectable amounts. In such case, a detectable amount of the rare element will be anything over zero. Where the rare element is normally found in the particular composition at a background level, then a detectable amount of the rare element will be an amount over the background level sufficient to differentiate the added material over the background level of rare element.

By rare elements, it is generally meant elements which are not found in crustal abundance at concentrations of greater than about 100 ppm. Suitable rare elements, and their crustal abundance, are: Ni - 80 ppm, Cu - 70 ppm, W - 69 ppm, Li - 65 ppm, N - 10 46 ppm, Ce - 46 ppm, Sn - 40 ppm, Y - 28 ppm, Nd - 24 ppm, Nb - 24 ppm, Co - 23 ppm, La - 18 ppm, Pb - 16 ppm, Ga - 15 ppm, Mo - 15 ppm, Th - 12 ppm, Cs - 7 ppm, Ge - 7 ppm, Sm - 6.5 ppm, Gd - 6.4 ppm, Be - 6 ppm, Pr - 5.5 ppm, Se - 5 ppm, As - 5 ppm, Hf - 4.5 ppm, Dy - 4.5 ppm, U - 4 ppm, B - 3 ppm, Yb - 2.7 ppm, Er - 2.7 ppm, Ta - 2.1 ppm, Br - 1.6 ppm, Ho - 1.2 ppm, Eu - 1.1 ppm, Sb - 1 ppm, Tb - 0.9 ppm, Lu - 0.8 ppm, Tl - 0.6 ppm, Hg - 0.5 ppm, I - 0.3 ppm, Bi - 0.2 ppm, Tm - 0.2 ppm, Cd - 0.15 ppm, Ag - 0.1 ppm, In - 0.1 ppm, Se - 0.09 ppm, Pd- 0.01 ppm, Pt - 0.005 ppm, Au - 0.005 ppm, He - 0.003 ppm, Te - 0.002 ppm, Rh - 0.001 ppm, Re - 0.001 ppm, Ir - 0.001 ppm, Os - 0.001 ppm, and Ru 0.001 ppm. Rare elements which are members of the lathanide series are preferred, since they are readily detectable. In some cases, the rare element will be present in the chemical composition at greater than the above levels, to facilitate identification in the event that the composition or a product from the composition has become dispersed over the ground surface, such as by explosion. Generally speaking, the rare elements are present in the chemical composition being tagged in an amount in the range of from about 0.001 to about 100 ppm per rare element present, based on elemental weight.

It is also within the scope of this invention to form unique tagging agensts based on the weight ratios of the rare elements present. For example, tagging agents containing the same rare elements but at different weight ratios can be easily differentiated by using conventional analysis techniques.

By natural isotopic abundance, it is intended to mean that the isotopic makeup of the particular rare elements employed has not been altered. This determination can be easily made using mass spectrometer techniques and available data.

By dispersed, it is intended to mean that the tagging agents are uniformly distributed throughout the composition. Where the composition is a liquid, this is easy to accomplish by using soluble forms of the rare elements in the particular liquid composition. Where the composition is a particulate, the dispersal can be either on the macroscopic or microscopic level, but it preferable that the dispersal be on the microscopic level. However, for some applications, it is contemplated that the at least two rare elements be contained in a bead. Use of a bead could facilitate collection of the tagging agents after a bombing. The bead comprises the at least two rare elements dispersed in a continuous matrix. The matrix can be formed from a wide variety of materials. A ferromagnetic material, a glass material, and a polymeric material are exemplary. The ferromagnetic beads could be collected using a magnet after a bombing. A colored glass bead could be collected visually. Polymer beads could be separated after an explosion using sink and float techniques. Preferably, however, the at least two rare elements are impregnated throughout the chemical composition, such as by being impregnated onto particles of the composition from a slurry liquid or by being sprayed onto particles of the composition.

Because there are a large number of rare elements, there is an extremely large number of possible subcombinations of rare elements. It is therefore feasible to assign distinct subcombinations to chemical commodities, based on batch or chemical manufacturer, for example. Generally speaking, it is anticipated that the number of rare elements employed in a tagging agent will range from two to about 10, preferably in the range of from 3 to 10. Records can be kept by particular manufacturers, and/or reported to a centralized recordkeeping location, depending on the need being served, to enable the manufacturer of a particular composition to be determined.

In another embodiment of the invention, there is provided a method for tagging a chemical composition with a tagging agent. The method is carried out by dispersing a tagging agent throughout the chemical composition. The tagging agent contains at least two different rare elements of the periodic table which are foreign to the chemical composition. Each rare element is dispersed in the chemical composition in a detectable amount and has a natural isotopic distribution. The method is well adapted for producing the composition previously discussed.

In another embodiment of the invention, there is provided a composition of matter which is useful as a tagging agent. The composition comprising a carrier liquid containing soluble forms of at least two different rare elements. The rare elements are selected from the periodic table and have a naturally occurring isotopic distribution. The soluble forms of the rare elements are dissolved in the carrier liquid. The composition is well suited for use in the method previously discussed. Generally speaking, the carrier liquid will comprise an aqueous solution. A wide range of rare element compositions can be solubilized in the solution, such as salts, chelates or organic compounds. For example, a wide range of nitrates, chlorides, acetates and citrates have sufficient solubility to be employed. Preferably, the tagging composition contains at least 3 different rare elements. Each of the rare elements is generally present at a concentration in the carrier liquid in the range of from about 1 ppm to about 100,000 ppm, based on elemental weight, usually in the range of from about 500 to about 50,000 ppm, based on elemental weight.

Where the chemical composition is a particulate material, the rare elements are preferably impregnated or deposited onto the material. The method is carried out by forming a slurry containing the particulate material in a carrier liquid. The slurry also contains a tagging agent containing at least two different rare elements. The rare elements are selected from the periodic table and have a naturally occurring isotopic distribution. Due to intimate contacts, the at least two different rare elements selected from the periodic table become dispersed in the particulate material. The particulate material is then separated from the carrier liquid to provide the tagged particulate material. The rare elements may also be deposited onto the particulate material by spraying a solution containing the rare elements onto the particles of the particulate.

The invention provides a technique which is highly useful for tagging explosive materials. In another embodiment of the invention, there is provided a method for determining the source of explosive material which has been used in an explosion. The explosion forms a blast residue. The method is carried out by collecting a portion of the blast residue. The collected portion is analyzed to identify a combination of rare elements present in the blast residue. The thus identified combination of rare elements in the blast residue is correlated with a combination of rare elements which have been used in a tagged explosive material. The source of the tagged explosive material can then be determined, based on the combination of rare elements present.

Usually, the blast residue includes unconsumed explosive material. The tagging agents can be recovered from the unconsumed explosive material as well as from the explosion products.

Where a bombing has occurred, the area directly beneath the bomb is referred to a ground zero. Blast residue is driven into the earth at the ground zero location, from where it is relatively easily recovered. It is thus preferable to recover the blast residue at ground zero.

The blast residue or explosive material can be tagged, if desired, with a tagging agent composition as herein described to establish chain of custody.

The analysis to determine the identity of the tagging agents can be performed using a wide variety of techniques. A combination of inductively coupled plasma analysis with further analysis by mass spectroscopy is preferred.

For practical applications, a field analysis followed by a confirmatory rigorous laboratory analysis is the preferred mode for performing the analysis.

EXAMPLE 1

A 100,000 dead weight ton tanker is filled with crude oil for shipment to its desired location. About one eighth of one quart of deuterated octane of the formula $CH_2DCH_2CH_2CH_2CH_2CH_2CH_2CH_3$ is added to the crude oil. This provides approximately one part per billion of deuterated octane in the tanker. Upon arrival at its destination point, a sample of crude oil is removed from the tanker. Analysis by gas chromatography or mass spectroscopy indicates if the crude oil at the destination point is the same as the crude oil shipped from the origination port.

EXAMPLE 2

A 100,000 dead weight ton tanker is filled with crude oil for shipment to its desired location. About one eighth of one quart of deuterated acetone of the formula $CH_2DCOCH_2D$ is added to the crude oil. This provides approximately one part per billion of deuterated acetone in the tanker. A spill is located. A sample of the spill is removed and analyzed by either mass spectroscopy or gas chromatography. Matching of the data of the isotope $CH_2DCOCH_2D$ with the data from the spill will be determinative if the oil spill is attributed to the 100,000 dead weight ton tanker.

EXAMPLE 3

A 100,000 dead weight ton tanker is filled with crude oil for shipment from port A to its desired location, port B. About two and one-half quarts of a mixture of tetrafluoroethylene, chloroform, and trichloroethylene is added to the crude oil at port A. This provides approximately 20 parts per billion of halogenated hydrocarbon mixture in the oil. The ratio of tetrafluoroethylene:chloroform:trichloroethylene is 1:3:7.

A large spill of crude oil appears on the beaches of Galveston, Tex. and a sample is taken to identify the source of the crude oil spill. An analysis reveals that the crude oil contains one pans per billion of a mixture of tetrafluoroethylene, chloroform, and trichlorethylene in the ratio 1:3:7. Consequently, the spillage is conclusively identified as originating from the 100,000 dead weight ton crude oil tanker.

Having described the invention above, various modifications of the techniques, procedures, material and equipment will be apparent to those in the art. It is intended that all such variations within the scope and spirit of the appended claims be embraced thereby.

What is claimed is:

1. A chemical composition which contains a tagging agent uniformly dispersed therein at the atomic level, said tagging agent containing at least two different rare elements of the periodic table which are foreign to the chemical composition and are present in said chemical composition in a detectable amount and at natural isotopic distribution.

2. A chemical composition as in claim 1 which comprises a chemical commodity wherein each rare element is naturally occurring at a crustal abundance of less than 100 ppm and the chemical commodity is in the form of a particulate solid.

3. A chemical commodity as in claim 2 wherein the at least two rare elements are impregnated from solution throughout the particulate solid.

4. A chemical commodity as in claim 3 wherein the rare elements are present in the particulate solid in an amount in the range of from about 0.001 to about 100 ppm per rare element present, based on elemental weight.

5. A chemical commodity as in claim 2 wherein the at least two different rare elements are selected from the group consisting of Ni, Cu, W, Li, N, Ce, Sn, Y, Nd, Nb, Co, La, Pb, Ga, Mo, Th, Cs, Ge, Sm, Gd, Be, Pr, Se, As, Hf, Dy, U, B, Yb, Er, Ta, Br, Ho, Eu, Sb, Tb, Lu, Tl, Hg, I, Bi, Tm, Cd, Ag, In, Se, Pd, Pt, Au, He, Te, Rh, Re, Ir, Os, and Ru.

6. A chemical commodity as in claim 5 which comprises an explosive.

7. A chemical commodity as in claim 5 which comprises a nitrate.

8. A chemical commodity as in claim 7 which comprises at least 99 percent by weight of ammonium nitrate.

9. A method for tagging a chemical composition, said method comprising dispersing a tagging agent in solution form throughout said chemical composition, wherein the tagging agent contains at least two different rare elements of the periodic table which are foreign to the chemical composition, each rare element being dispersed at the atomic level in a detectable amount and having a natural isotopic distribution.

10. A method as in claim 9 wherein chemical composition comprises a particulate chemical commodity and the tagging agent is dispersed throughout the particulate chemical commodity by impregnating the particulate chemical commodity with a solution containing the at least two rare elements in a solubilized state.

11. A method as in claim 9 wherein the chemical composition comprises a particulate chemical commodity and the tagging agent is dispersed throughout the particulate chemical commodity by spraying the particulate commodity with a solution containing the at least two rare elements in a solubilized state.

* * * * *